ent [19]
Heitz et al.

[11] 4,327,035
[45] Apr. 27, 1982

[54] PROCESS FOR THE PREPARATION OF CARBONIC ACID ESTERS

[75] Inventors: Walter Heitz, Kirchhain; Peter Ball, Neu Oetting, both of Fed. Rep. of Germany

[73] Assignee: Bayer Aktiengesellschaft, Leverkusen, Fed. Rep. of Germany

[21] Appl. No.: 112,893

[22] Filed: Jan. 17, 1980

[30] Foreign Application Priority Data

Jan. 30, 1979 [DE] Fed. Rep. of Germany ....... 2903506

[51] Int. Cl.$^3$ .............................................. C07C 68/00
[52] U.S. Cl. ................................. 260/463; 260/340.2; 260/347.8; 528/370
[58] Field of Search ........................................ 260/463

[56] References Cited

U.S. PATENT DOCUMENTS 2,370,571 2/1945 Muskat et al. ..................... 260/463
2,834,799 5/1958 Sowa ................... 260/463
3,642,858 2/1972 Frevel et al. ........................ 260/463

OTHER PUBLICATIONS

P. Ball et al., Angewandte Chemie (1980), 742–743.

A. Paquin, Z. Naturforschung 1, 518–523 (1946), The Conversion of Urea with Alcohols.

Wagner and Zook, Synthetic Organic Chemistry (1953), p. 647.

Smith, Open–Chain Nitrogen Compounds, vol. 1, p. 261 (1965), Benjamin, Inc. N.Y.

Primary Examiner—Anton H. Sutto
Attorney, Agent, or Firm—Gene Harsh; Lawrence S. Pope; Aron Preis

[57] ABSTRACT

The present invention relates to a process for the preparation of carbonic acid esters of monoalcohols or polyalcohols, which is characterized in that ureas are reacted with monoalcohols or with polyalcohols in the molar ratio of at least 1:2, in the presence of a catalyst, at reaction temperatures between 120° C. and 270° C.

Accordingly, the present invention also relates to a process for the preparation of oligocarbonates and polycarbonates, which is characterized in that ureas are reacted with primary dialcohols in the molar ratio of about 1.5:1 to about 1:1.5, together with monoalcohols, in the presence of catalysts at reaction temperatures between 120° C. and 270° C.

3 Claims, No Drawings

PROCESS FOR THE PREPARATION OF CARBONIC ACID ESTERS

The present invention relates to a process for the preparation of carbonic acid esters of monoalcohols or polyalcohols, which is characterised in that ureas are reacted with monoalcohols or with polyalcohols in the molar ratio of at least 1:2, in the presence of a catalyst, at reaction temperatures between 120° C. and 270° C.

Compared to the known reaction of highly activated ureas with alcohols and phenols (see Staab, Angew.-Chem. 68 (1956), page 754, Staab, Liebigs Ann.Chem. 609 (1957), page 75 et seq. and page 83 et seq., K. Schlögl and H. Woidich, Mh.Chem. 87 (1956) 679 and J. Derkosch, K. Schlögl and H. Woidich, Mh.Chem. 88 (1957) 35 and French Patent Specification 1,208,196), it is surprising that even non-activated ureas can be reacted with alcohols in accordance with the process of the invention, as such reaction hitherto only proceeded to the urethane stage (see Zeitschrift für Naturforschung, Vol. 1, 1946, pages 518 et seq.).

Preferred monoalcohols and polyalcohols are primary alcohols which may contain any desired number of C atoms. Suitable alcohols are aliphatic, cycloaliphatic, araliphatic and heterocyclic alcohols. Polyalcohols, in the sense of the present invention, are, for example, those with 2 to 3 alcoholic OH groups, and given an appropriate spacing of the alcoholic OH groups in the molecule, cyclic carbonic acid esters may result.

The suitable monoalcohols preferably have 1 to 20 C atoms.

Examples of the monoalcohols are methanol, ethanol, propanols, butanols, pentanols, hexanols, octanols, stearyl alcohol, methylolcyclohexane, benzyl alcohol, 2-phenylethanol, 2-naphthylethanol, furfuryl alcohol and the like.

Suitable polyalcohols preferably have 5 to 20 C atoms.

Examples of the polyalcohols are hexane-1,6-diol, decanediols, 1,4-dimethylolcyclohexane, 1,4-dimethylolbenzene, 3(4), 8(9)-bis-(hydroxymethyl)-tricyclo[5,2,1,0$^{2:6}$]decane

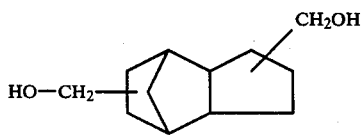

and bis-hydroxymethyl-tetrahydrofuranes, and the like.

Ureas which are suitable, according to the invention, are, in addition to urea itself, ureas which are mono-, di-, tri- or tetra-substituted by hydrocarbon radicals, preferably ureas of the following formula I

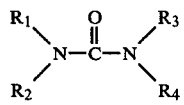

wherein $R_1$ to $R_4$ are H or hydrocarbon radicals with 1 to 18 C atoms, which may either contain hetero-atoms, such as O, N or S or may be linked to form heterocyclic rings, in which latter case it is only possible for $R_1$ to be linked to $R_2$ and/or for $R_3$ to be linked to $R_4$, with the proviso that the amines formed during the reaction must have a boiling point of less than 150° C., preferably less than 120° C. $R_1$ to $R_4$ may be identical or different.

Suitable hydrocarbon radicals are alkyls, alkoxyalkyls, aryls, aralkyls and cycloalkyls.

Examples of ureas which are suitable according to the invention are urea, mono-, di-, tri- and tetra-methylurea, mono-, di-, tri- and tetra-ethylurea, mono- and di-phenylurea, benzylurea, cyclohexylurea and the like.

Examples of catalysts which are suitable according to the invention are compounds of main groups and sub-groups 1 to 6, and of sub-groups 7 and 8, of the periodic table of the elements (see Hollemann-Wiberg, Lehrbuch der Anorganischen Chemie (Textbook of Inorganic Chemistry), 37–39th edition, published by Walter De Gruyter u. Co., Berlin 1956).

Compounds of main group 1 and sub-group 1 which are suitable according to the invention are both salt-like and covalent compounds of the metals of these groups of the periodic table, such as LiBr, butyl-lithium, LiCl, LiI, NaOCH$_3$, CuCl, AgOCO—CH$_3$ and the like.

Compounds of main group 2 and sub-group 2 which are suitable according to the invention are both salt-like and covalent compounds of the metals of these groups of the periodic table, such as MgCl$_2$, Be(O—CO—CH$_3$)$_2$, Grignard compounds, ZnCl$_2$, ZnSO$_4$, Mg(OC$_2$H$_5$)$_2$ and the like.

Compounds of main group 3 and sub-group 3 which are suitable according to the invention are, in particular, covalent compounds of the elements of these groups of the periodic table, such as B-(-O—C$_6$H$_5$)$_3$, B(C$_6$H$_5$)$_3$, Al(OR)$_3$ (R=an aliphatic or aromatic hydrocarbon radical), and the like.

Compounds of main group 4 and sub-group 4 which are suitable according to the invention are, in particular, covalent compounds of the elements of these groups of the periodic table, such as orthotitanates (for example tetrabutyl-orthotitanate), orthostannates (for example tetraphenyl-orthostannate) and the like.

Compounds of main group 5 and sub-group 5 which are suitable according to the invention are, in particular, covalent compounds of the elements of these groups of the periodic table, such as amines (for example diazabicyclooctane), phosphines (for example triphenylphosphine and tri-n-octylphosphine), phosphine oxides (for example triphenylphosphine oxide) and the like.

Compounds of main group 6 and sub-group 6 which are suitable according to the invention are both covalent and salt-like compounds of the elements of these groups of the periodic table, such as thioethers (for example diphenyl sulphide), thiolates (for example Na thiophenolate) and the like.

Compounds of sub-group 7 which are suitable according to the invention are both covalent and salt-like compounds of the elements of this group of the periodic table (for example manganese(II) acetate).

Compounds of sub-group 8 which are suitable according to the invention are both covalent and salt-like compounds of the elements of this group of the periodic table (for example iron(III) acetylacetonate).

Particularly preferred catalysts for the process according to the invention are combinations of the above-mentioned compounds, it being necessary to balance the electron donor and electron acceptor properties of the catalyst combination with one another, that is to say combinations of electron donors and electron acceptors.

Examples of such combinations are aluminium alcoholates used in combination with amines, phosphines or phosphine oxides, lithium salts used in combination with orthotitanates or magnesium alcoholates used in combination with thioethers.

The catalysts which are suitable according to the invention are employed in amounts of $10^{-3}$ to 5 mol %, relative to the number of mols of the particular ureas employed, and these figures apply both to the use of individual catalysts and of catalyst combinations. The molar ratio of the two types of catalyst in the catalyst combinations can vary between 1:10 and 10:1.

To carry out the reaction according to the invention, the components, that is to say the urea, alcohol and catalyst, are warmed together, whilst stirring, to temperatures of at least 120° C. and then warmed slowly to 270° C. for 5 to 10 hours and allowed to finish reacting. The batch is then separated by distillation under gentle conditions, that is to say in vacuo at a lower temperature, and the carbonic acid ester is isolated; the yields are very good.

Since, in general, the alcohol component is employed in excess, the molar ratio of urea to alcohol varies between 1:2 and about 1:5, preferably between 1:2 and 1:3.

The carbonic acid esters prepared according to the process of the invention are known compounds and, as is known, can be used as solvents in organic chemistry and also as intermediate products and starting materials for a great diversity of chemical reactions.

In particular, they may be used, in a known manner (compare German Patent Specification No. 1,031,512, Example 1), for the synthesis of polycarbonates by reaction with diols.

The preparation of oligocarbonates and polycarbonates can be carried out in one step, using the process according to the invention, from the ureas mentioned, the monoalcohols mentioned and primary dialcohols, suitable dialcohols being aliphatic, cycloaliphatic and araliphatic dialcohols, with the proviso that virtually no formation of cyclic carbonates occurs under the process conditions.

Accordingly, the present invention also relates to a process for the preparation of oligocarbonates and polycarbonates, which is characterised in that ureas are reacted with primary dialcohols in the molar ratio of about 1.5:1 to about 1:1.5, together with monoalcohols, in the presence of catalysts at reaction temperatures between 120° C. and 270° C.

Preferably, in this reaction, the molar ratio of urea to dialcohols is about 1:1; the molar amount of monoalcohols, relative to the molar amount of dialcohols, depends on the particular chain length desired and since the monoalcohols are used in excess, such excess can be removed by distillation. Furthermore, the molecular weight of the oligocarbonates and polycarbonates can be regulated in a known manner by selection of the reaction temperature and of the reaction time. Accordingly, oligocarbonates and polycarbonates of primary dialcohols, having a range of molecular weights, can be prepared in a simple manner by the process according to the invention.

As far as the ureas, monoalcohols and catalysts suitable for the preparation of oligocarbonates and polycarbonates according to the invention are concerned, the definitions given at the outset in relation to the preparation, according to the invention, of carbonic acid esters again apply.

The preparation, according to the invention, of oligocarbonates and polycarbonates requires between 2 and 10 hours, depending on the batch and on the temperature settings. The desired end point of the reaction can in each case be detected, for example, by viscometry.

Preferred suitable primary dialcohols are those with 5 to 20 C atoms; examples are those already mentioned at the outset in connection with the preparation, according to the invention, of carbonic acid esters, such as hexane-1,6-diol or 1,4-dimethylol-cyclohexane.

The remaining reaction conditions of the preparation of the oligocarbonates or polycarbonates, that is to say the nature and amount of the catalysts to be employed, and the temperature settings, correspond to those of the preparation of the monomeric carbonic acid esters, already described.

The oligocarbonates and polycarbonates obtained according to the process of the invention are known in principle and are suitable for use, in a known manner, for the production of mouldings and films, and as coatings and additives for other plastics. Accordingly, the oligocarbonates and polycarbonates obtainable according to the invention are suitable for the known fields of use of the thermoplastic polycarbonates, namely, say, in the case of the oligocarbonates as secondary plasticisers in, for example, PVC, and as modifiers of high-molecular thermoplastic polycarbonates, for example according to U.S. Pat. No. 3,166,606.

EXAMPLE 1

Preparation of a low-molecular carbonic acid ester 30.95 g of urea, 185.0 g of 2-ethylhexan-1-ol, 0.69 g of triphenylphosphine and 2.6 ml of a 20% strength solution of diisobutyl-aluminium hydride in toluene were warmed together. At about 150° C., the whitish turbid mixture began to boil. The temperature was raised to 192° C. in the course of 1.5 hours; at this point in time, 10.46 g of NH$_3$ had separated out. The temperature was raised to 269° C. over the course of a further 7 hours; at that stage, 16.23 g of NH$_3$ had been eliminated and 56.02 g of liquid, consisting of 2-ethylhexan-1-ol apart from a small amount of dissolved urethane, urea and NH$_3$, had been distilled off. The mixture was then fractionated; this gave a fraction of 20.67 g of boiling point 81.5° C./14 mm Hg (alcohol) and a fraction of 128.80 g, of boiling point 98°–102° C./~0.05 mm Hg (bis-(2-ethylhexyl)-carbonate); yield 87.9%, relative to urea employed.

|          |     | calculated | found |
|----------|-----|------------|-------|
| Analysis | % C | 71.28      | 72.59 |
|          | % H | 11.96      | 11.92 |
|          | % O | 16.76      | 16.54 |

EXAMPLE 2

Preparation of a polycarbonate 15 g of urea, 30.26 g of 1,4-bis-(hydroxymethyl)cyclohexane, 34 g of isononyl alcohol, 0.34 g of triphenylphosphine and 1.2 ml of a 20% strength solution of diisobutyl-aluminium hydride in toluene were fused together, and warmed. At about 170° C., the melt was almost clear and began to boil vigorously. The temperature was raised to 225° C. over the course of 45 minutes;

at this point in time, 4.92 g of NH₃ had been eliminated. The temperature was then raised continuously, over the course of 2.5 hours, to 260° C.; at that stage, 7.37 g of NH₃ had been eliminated.

After cooling the melt to 150° C., a waterpump vacuum was applied and the temperature was raised to 260° C. over the course of 30 minutes; in the course thereof, the isononyl alcohol distilled off and the melt became viscous. The reaction mixture was then warmed for 3 hours at 250° C. under an oil pump vacuum, during which the remainder of the isononyl alcohol, some diol and di-isononyl carbonate distilled off. 32.78 g of a clear, non-crystalline polycarbonate remained ($M_n \cong 11,000$).

The determination of the $M_n$ was carried out by vapour pressure osmometry. The polycarbonate had a $\eta_{rel}$ (measured on an 0.5% strength solution in methylene chloride at 25° C.) of 1.26.

EXAMPLE 3

10 g of urea, 70 g of isononanol, 0.5 ml of tetrabutyl orthotitanate and 0.2 g of LiBr were reacted analogously to Example 1. Yield of di-isononyl carbonate: 57%.

EXAMPLE 4

10 g of urea, 70 g of 2-ethylhexan-1-ol, 0.57 g of magnesium acetate and 1.03 g of triphenylphosphine were reacted analogously to Example 1. The yield of bis-(2-ethylhexyl)-carbonate was 41%.

EXAMPLE 5

10 g of urea, 70 g of 2-ethylhexan-1-ol, 1.01 g of iron-(III) acetylacetonate and 0.71 g of triphenylphosphine were reacted analogously to Example 1. The yield of carbonic acid ester was 76%.

EXAMPLE 6

10 g of urea, 70 g of 2-ethylhexan-1-ol, 0.5 g of chromium(III) acetate and 1.0 g of triphenylphosphine were reacted analogously to Example 1. The yield of carbonic acid ester was 43%.

What is claimed is:

1. Process for the preparation of carbonic acid esters of monoalcohols or polyalcohols characterized in that ureas of the formula

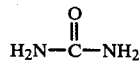

are reacted with C₁–C₂₀ monoalcohols or with C₅–C₂₀ polyalcohols in the molar ratio of at least 1:2 in the presence of a catalyst selected from the group consisting of
  (i) saltlike or covalent compounds of main groups 1 and 2 and subgroups 1, 2, 3, 4, 5, 6, 7 and 8 of the Periodic Table of the elements;
  (ii) orthostannates, amines, phosphines, phosphineoxides, thioethers, thiolates, B(O—C₆H₅)₃, B(C₆H₅)₃ and Al(OR)₃ where R is an aliphatic or an aromatic hydrocarbon radical;
  (iii) saltlike or covalent compounds of main groups 4, 5, and 6 in combination with any of (i) or (ii);
  (iv) combination of any member of (i) with any other of (i) or (ii);
  (v) combination of any member of (ii) with any other of (ii); said catalyst amounting to between about $10^{-3}$ and 5 mol percent relative to the number of mols of said urea, said combinations characterized in that they combine electron donors and electron acceptors at reaction temperatures between 120° and 270° C. and at a reaction time of 5 to 10 hours.

2. Process for the preparation of oligocarbonates and polycarbonates characterized in that ureas of the formula

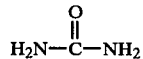

are reacted with C₅–C₂₀ primary dialcohols in the molar ratio of from about 1.5:1 to about 1:1.5 and with C₁–C₂₀ monoalcohols in the presence of a catalyst selected from the group consisting of
  (i) saltlike or covalent compounds of main groups 1 and 2 and subgroups 1, 2, 3, 4, 5, 6, 7 and 8 of the Periodic Table of the elements;
  (ii) orthostannates, amines, phosphines, phosphineoxides, thioethers, thiolates, B(O—C₆H₅)₃, B(C₆H₅)₃ and Al(OR)₃ where R is an aliphatic or an aromatic hydrocarbon radical;
  (iii) saltlike or covalent compounds of main groups 4, 5 and 6 in combination with any of (i) or (ii);
  (iv) combination of any member of (i) with any other of (i) or (ii);
  (v) combination of any member of (ii) with any other of (ii); said catalyst amounting to between about $10^{-3}$ and 5 mol percent relative to the number of mols of said urea, said combinations characterized in that they combine electron donors and electron acceptors at reaction temperatures between 120° and 270° C.

3. Process according to claim 2, characterised in that the molar ratio of urea to dialcohol is about 1:1.

* * * * *